United States Patent [19]

Dinerstein et al.

[11] Patent Number: 5,248,825
[45] Date of Patent: Sep. 28, 1993

[54] CALCIUM UPTAKE INHIBITORS

[75] Inventors: Robert J. Dinerstein, Cincinnati; Jeffrey S. Sabol, Loveland; Keith A. Diekema, West Chester, all of Ohio

[73] Assignee: Merrell Dow Pharmaceuticals Inc., Cincinnati, Ohio

[21] Appl. No.: 892,440

[22] Filed: Jun. 1, 1992

Related U.S. Application Data

[63] Continuation of Ser. No. 585,759, Sep. 20, 1990, abandoned.

[51] Int. Cl.$^5$ .................. C07C 211/43; C07C 49/794
[52] U.S. Cl. ................................ 564/305; 568/331; 568/334
[58] Field of Search ............... 568/331, 334; 564/305

[56] References Cited

U.S. PATENT DOCUMENTS

| | | | |
|---|---|---|---|
| 2,961,468 | 11/1960 | Becke et al. | 568/334 X |
| 3,409,424 | 11/1968 | Brewbaker et al. | 568/331 |
| 3,678,044 | 7/1972 | Adams | 568/334 X |
| 4,279,930 | 7/1981 | Hall et al. | 564/305 X |
| 4,929,741 | 5/1990 | Fischli et al. | 568/331 |

FOREIGN PATENT DOCUMENTS

| | | |
|---|---|---|
| 82081591 | 12/1971 | France . |
| 72387956 | 11/1978 | France . |
| 91395563 | 5/1975 | United Kingdom . |

OTHER PUBLICATIONS

Gerko et al., *Chem Abs.*, "Spectral . . . " vol. 89, 146012q, 1978.
Jong et al., Chem Abs, "Intramolecular . . . " vol. 113, 97350b, 1990.
Chen, F., et al., Tai-Wan K'o Hsueh 26(3-4), 98-9 (1972); Chem. Abst, 78(23), 147754t, Jun. 11, 1979.
Durinda, J., et al., Cesk. Farm. 26(5), 140-9 (1977); Chem. Abst. 88(1), 6671h, Jan. 2, 1978.
Boedeker, J., et al., J. Prakt. Chem. 324(1), 15-20 (1982); Chem. Abst. 97(3), 23594p, Jul. 19, 1982.
Sacchar, S. P., et al, Bokin Bobai 11(5), 269-74 (1983); Chem. Abst. 99(7) 139709a, Oct. 24, 1983.
Minn, K., 8th Int. Conf. on Organic Synthesis (IUPAC), Helsinki, Jul. 23-27 1990.
Kundu et al., Chemical Abstracts, vol. 113(3): Jul. 16, 1990, abstract No. 23842s.
Kundu et al., Chemcial Abstracts, vol. (9): Aug. 29, 1988, abstract No. 73389n.

*Primary Examiner*—Marianne M. Cintins
*Assistant Examiner*—Michael B. Hydorn
*Attorney, Agent, or Firm*—Kenneth J. Collier

[57] ABSTRACT

This invention relates to 1-phenyl-3-phenyl-2-propyne-1-ones, the use of these compounds as calcium uptake inhibitors in leukocytes and thrombocytes, and pharmaceutical compositions containing these compounds as active ingredients, and the process of their preparation.

10 Claims, 1 Drawing Sheet

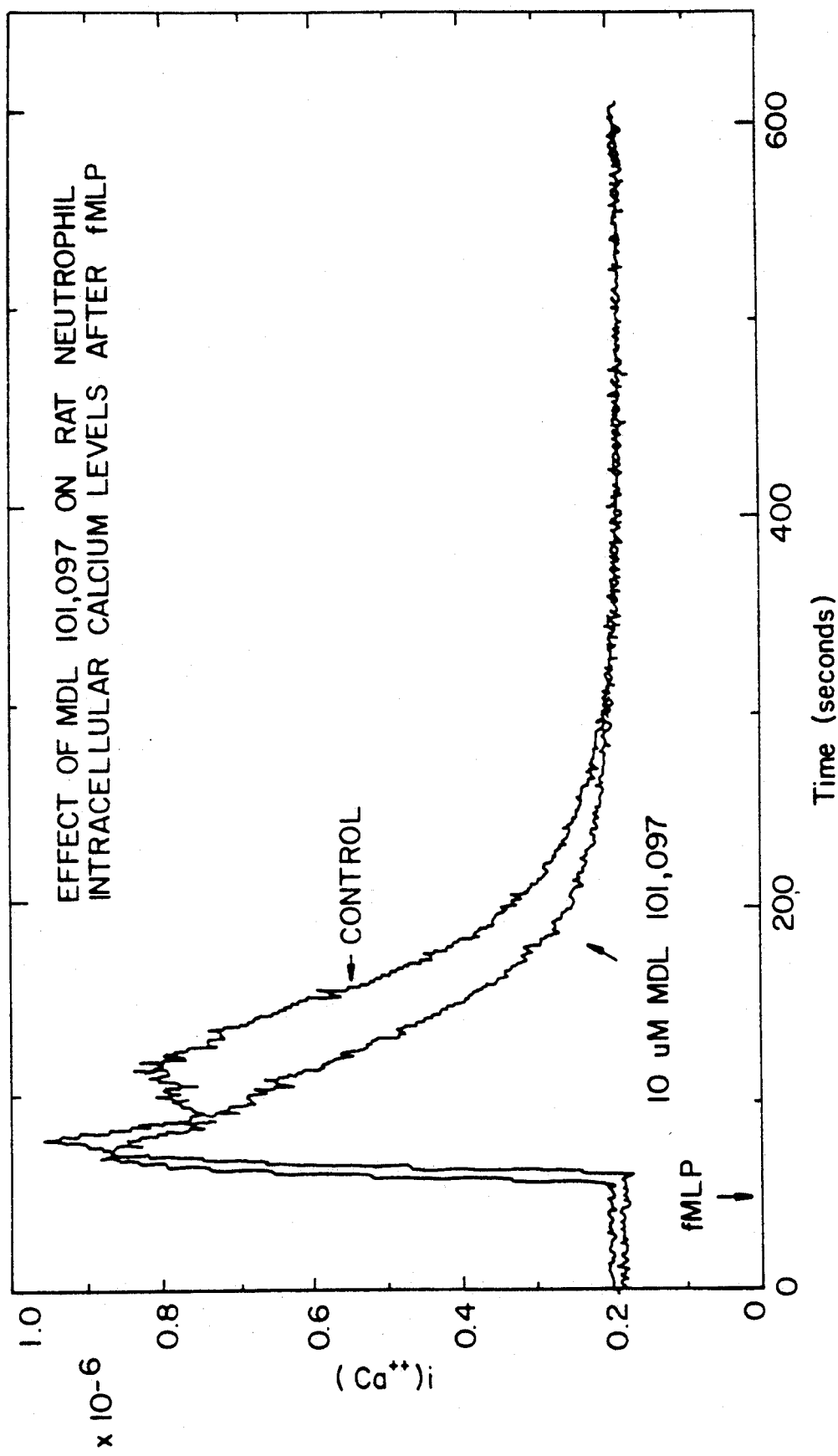

CALCIUM UPTAKE INHIBITORS

CROSS-REFERENCE TO RELATED APPLICATION

This is a continuation of application Ser. No. 07/585,759, filed Sep. 20, 1990 now abandoned.

FIELD OF THE INVENTION

This invention relates to 1-phenyl-3-phenyl-2-propyne-1-ones, the use of these compounds as calcium uptake inhibitors in leukocytes and thrombocytes, and pharmaceutical compositions containing these compounds as active ingredients, and the process of their preparation.

BACKGROUND

Polymorphonuclear leukocytes (leukocytes) provide a principle means of defense against microbial infections. The response to invading microorganisms causes activation of cellular oxidative processes (production of hydroxyl radicals) and nonoxidative processes (digestive enzymes; myeloperoxidase, elastase, etc.) in order to effectively kill the microorganisms. However, the response of leukocytes to a foreign challenge can also cause destruction to host tissues and play an important part in the pathogenesis of a number of noninfectious disease conditions.

Leukocytes possess a wide variety of mechanisms that enable them to respond to foreign challenges which are initiated by cell surface receptors. Receptor activation or general cellular activation results in an altered cellular physiology causing the cell in itself to become "activated". The intracellular signaling molecules of activation are often referred to as second messengers, the first messengers being the extracellar activating ligands themselves.

One of the major second messengers in many cells is the calcium ion ($Ca^{+2}$). There are two general ways in which cell-surface receptors are known to generate intracellular calcium signals. One is by activating phospholipase C. This enzyme generates inositol trisphosphate which, in turn, releases stored calcium in the cell. Alternatively, cell receptors may open or close gated ion channels, letting calcium enter from outside the cell. $Ca^{+2}$ channels in the plasma membrane are of two types: (1) voltage sensitive calcium channels which are activated when a small and transient flux of ions briefly alter the voltage across the plasma membrane, or (2) receptor operated channels which are directly opened by receptor ligands. The first mechanism operates mainly in voltage sensitive cells such as neurons and muscle cells. Many cells, like leukocytes, are not primarily voltage sensitive cells but have cell-surface receptors that are functionally linked to receptor sensitive $Ca^{+2}$ channels in the plasma membrane. Binding of certain ligands activates these receptors, thereby opening the channels and allowing $Ca^{+2}$ to enter the cytosol, where it then functions as a second messenger.

When cells are activated, corresponding to an influx of $Ca^{+2}$, structures within the cell that bind $Ca^{+2}$ are responsive to such changes, depending on their relative affinity and specificity for calcium. A few $Ca^{+2}$ dependent proteins are known. The first such protein to be discovered and characterized was troponin C found in electrically active skeletal muscle cells. A later discovered calcium binding protein which is ubiquitous in both voltage and receptor sensitive cells is calmodulin.

Among the increasing number of cellular proteins known to be regulated by calmodulin in a $Ca^{+2}$ dependent manner are some forms of cyclic nucleotide phosphodiesterase and adenylate cyclase, as well as membrane bound calcium dependent ATPases, phosphorylase kinase, myosin light chain kinases, and their association with the spindles of the mitotic apparatus and the bundles of actin filaments. Although the total number of proteins that are calcium dependent or are affected by $Ca^{+2}$ dependent enzymes is not known it is clear that calcium is a requirement as a means of activating these processes.

When leukocytes are activated, a number of events can occur which are important in leading to intracellular calcium mediated disease states. For example leukocytes, primarily the neutrophils, are thought to play an integral part in the symptoms and tissue injury of the host in the following diseases; gout, rheumatoid arthritis, immune vasculitis, glomerulonephritis, inflammatory bowel disease, adult respiratory distress syndrome, emphysema, asthma, thermal injury associated with hemolysis, and malignant neoplasms at sites of chronic inflammation (Malech and Gallin; 1987). It therefore appears desirable to inhibit $Ca^{+2}$ uptake in leukocytes in order to alleviate or slow the progression of these immune and inflammatory diseases associated with calcium uptake.

$Ca^{+2}$ uptake in leukocytes and amelioration of immune and inflammatory diseases may also be extended to those diseases associated with the skin and dermal tissues. Included in the list of those topically related inflammatory diseases are those associated with skin and dermis, including neutrophil dermatoses, chronic dermatitis, psoriasis, contact dermatitis, atopic and seborrheic dermatitis, and acne.

Calcium is also an important mediator in thrombocytes (platelets) where it is well known that $Ca^{+2}$ is a required mediator in the intrinsic pathway of blood coagulation. For example, the $Ca^{+2}$ requirement in the blood clotting process and thrombus formation is well known and these processes can be inhibited in vitro, and to some degree in vivo, if chelating agents such as EDTA, citrate, or oxalate are added to bind $Ca^{+2}$. It is recognized that $Ca^{+2}$ plays an integral part of the fibrinolytic cascade and is an active mechanism by which the fibrinolytic response can be modulated therapeutically.

One of the primary functions of platelets occurs at a site of vascular injury wherein they form clot aggregates to close the wound. This response can also have a number of detrimental side effects, for example during ischemic reperfusion the thrombus formation can lead to occlusion of the artery, to the extent of causing a myocardial infarction. It is therefore desirable in many instances to inhibit $Ca^{+2}$ uptake in platelets in order to control the thrombolytic response.

$Ca^{+2}$ entry into the cytosol, by various forms of receptor-mediated activation or by discharge of intracellular stores, is critically linked to certain cellular events of leukocyte activation and platelet aggregation. Altering pathways of $Ca^{+2}$ mobilization provides a mechanism to modulate the responses of leukocytes and platelets. Therefore compounds that inhibit $Ca^{+2}$ mobilization might be expected to reduce $Ca^{+2}$ dependent disease processes associated with leukocyte activation and inhibition in immune and inflammatory diseases and in problems involving platelet aggregation in certain thrombolytic conditions.

SUMMARY OF THE INVENTION

The present invention relates to novel 1-phenyl-3-phenyl-2-propyne-1-one derivatives which are useful as inhibitors of calcium uptake in (1) leukocytes associated with acute and chronic inflammatory and immune diseases, including related (2) disease of the skin and dermal tissues. Finally, this invention relates also to the use of 1-phenyl-3-phenyl-2-propyne-1-one derivatives in the treatment of calcium dependent (3) processes of the thrombolytic system.

This inventions relates to compounds of the formula:

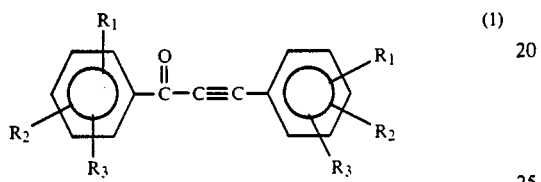

(1)

wherein $R_1$, $R_2$ and $R_3$ each time taken are independently hydrogen; $C_1$-$C_6$ alkyl; $C_1$-$C_6$ alkoxy; halogen; —$N(Y_1)(Y_2)$, wherein $Y_1$ and $Y_2$ are each independently hydrogen or $C_1$-$C_6$ alkyl; or $X_z$—(Ar)—$(CH_2)_n$—O—, wherein Ar is phenyl or napthyl, n=0 or 1 $X_2$=hydrogen, $C_1$-$C_6$ alkoxy or —$N(Y_1).(Y_2)$, wherein $Y_1$ and $Y_2$ are as previously defined and Z=0, 1, 2;

or a pharmaceutically acceptable salt thereof.

The present invention also provides a method of inhibiting calcium uptake in a patient in need thereof comprising administration of a therapeutically effective inhibitory amount of a compound of formula (1).

BRIEF DESCRIPTION OF THE DRAWING

FIG. 1 depicts the effect on intracellular calcium levels utilizing a compound of the invention.

DETAILED DESCRIPTION OF THE INVENTION

As used herein, the term "$C_1$-$C_6$ alkyl" refers to a saturated straight or branched chain hydrocarbyl radical of one one to six carbon atoms. Included within the scope of this term are methyl, ethyl, n-propyl, isopropyl, n-butyl, isobutyl, sec-butyl, t-butyl, n-pentyl, n-hexyl, and the like. The term "$C_1$-$C_6$ alkoxy" refers to methoxy, ethoxy, propoxy and the like. It is also understood that the term $X_z$—(Ar)—$(CH_2)_n$—O— specifically includes benzyloxy, (4-methoxy)benzyloxy, (4-dimethylamino)benzyloxy, and the like. The term "halogen" refers to a fluorine, chlorine, bromine, or iodine atom.

The compounds of formula (1) can be prepared by utilizing procedures and techniques well known and appreciated by one of ordinary skill in the art. A general synthetic scheme for preparing compounds of formula (1) is set forth in Scheme A, wherein all substituents, unless otherwise indicated, are previously defined.

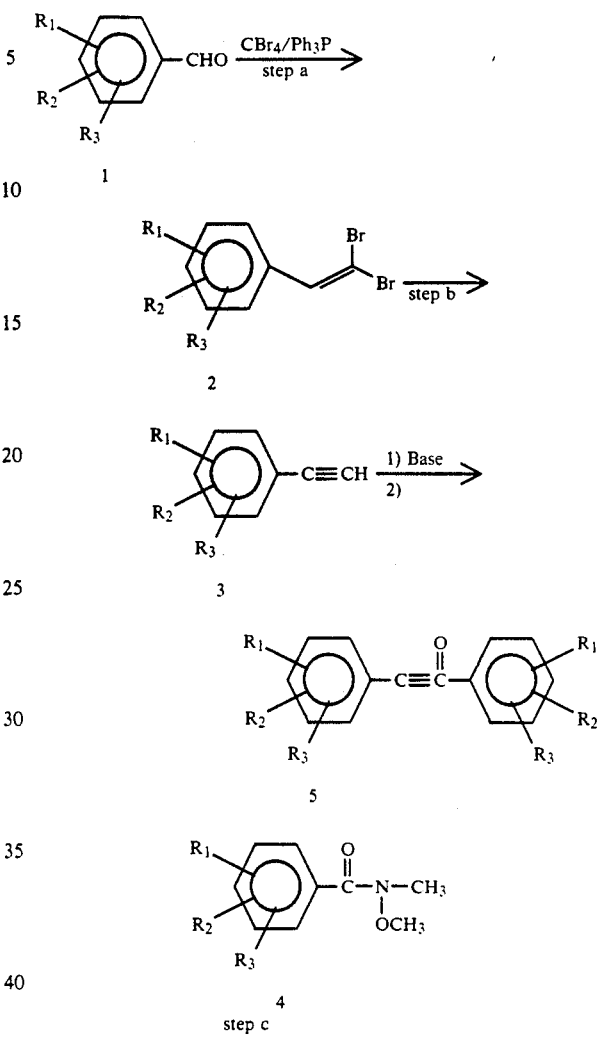

Scheme A

In general, a 1-phenyl-3-phenyl-2-propyne-1-one compound of structure 5 can be prepared according to Scheme A is a 3-step process.

In step a, the appropriate 2′,2′-dibromostyrene compound of structure 2 can be prepared by reacting the appropriate benzaldehyde compound of structure 1 with carbon tetrabromide and triphenylphosphine in a suitable aprotic solvent, such as methylene chloride.

Ins step b, the appropriate phenylacetylene compound of structure 3 can be prepared by reacting the appropriate 2′,2′-dibromostyrene compound of structure 2 with a non-nucleophilic base, such a n-butyllithium, in a suitable aprotic solvent, such as tetrahydrofuran.

In step c, the appropriate 1-phenyl-3-phenyl-2-propyne-1-one compound of structure 5 can be prepared by first reacting the appropriate phenylacetylene compound of structure 3 with a non-nucleophilic base, such as n-butyllithium, lithium hexamethyldisilazane, or lithium diisopropylamide, in a suitable aprotic solvent, such as tetrahydrofuran. The corresponding lithium acetylide can then be reacted with the appropriate N-methoxy-N-methylbenzamide (Weinreb reagent) of structure 4 to give the corresponding 1-phenyl-3-phenyl-2-propyne-1-one compound of structure 5.

Alternatively, the appropriate 1-phenyl-3-phenyl-2-propyne-1-one compound of structure 5 can be prepared by combining step b and step c. For example, the appropriate lithium acetylide compound obtained from step b can be used directly in the reaction with the appropriate N-methoxy-N-methylbenzamide (Weinreb reagent) of structure 4 to give the corresponding 1-phenyl-3-phenyl-2-propyne-1-one compound of structure 5.

Starting materials for use in the general synthetic procedure outlined in Scheme A are readily available to one of ordinary skill in the art. For example, certain N-methoxy-N-methylbenzamides are described in *Tetrahedron Letters*, 22(39), 3815-18 (1981).

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mol" refers to moles; "mL" refers to milliliters; "bp" refers to boiling point; "°C." refers to degrees Celsius; "mm Hg" refers to millimeters of mercury; "mp" refers to melting point; "mg" refers to milligrams; "μM" refers to micromolar; "μg" refers to micrograms.

EXAMPLE 1

1-Phenyl-3-(3,4,5-trimethoxyphenyl)-2-propyne-1-one

Step a: 3,4,5-Trimethoxy-2',2'-dibromostryene

Mix carbon tetrabromide (3.32 g, 10 mmol) and methylene chloride (7 mL) and cool to 0° C. Add, by dropwise addition, a solution of triphenylphosphine (5.24 g, 20 mmol) in methylene chloride (7 mL) and stir at 0° C. for 30 minutes. Add, by dropwise addition, 3,4,5-trimethoxybenzaldehyde (0.981 g, 5 mmol) in methylene chloride (10 mL). Remove the ice bath and stir at room temperature for 30 minutes. Pour onto silica gel and elute with 5% ethyl acetate/hexane. Evaporate the solvent in vacuo to yield 1.57 g of the title compound.

Step b and Step c:
1-Phenyl-3-(3,4,5-trimethoxyphenyl)-2-propyne-1-one

Place 3,4,5-trimethoxy-2',2'-dibromostryene (1.57 g, 4.46 mmol) and tetrahydrofuran (15 mL) under argon atmosphere and cool to −78° C. Add, by dropwise addition, n-butyllithium (5.85 mL of a 1.6M solution in hexane, 9.36 mmol) and stir for 1 hour at −78° C. Remove the cooling bath and stir for 1 hour at room temperature. Cool to −78° C. and add N-methoxy-N-methylbenzamide (1 mL, 6.6 mmol). Remove the cooling bath and stir at room temperature for 45 minutes. Partition between ethyl ether and water, separate the organic phase, dry, and evaporate the solvent in vacuo to yield a solid. Recrystallize (1:2 chloroform/hexane) to yield 0.48 g of the title compound; mp 158°-60° C.

EXAMPLE 2

1-Phenyl-3-[3-(4-methoxybenzyloxy)phenyl]-2-propyne-1-one

Step a: 3-(4-Methoxybenzyloxy)-2',2'-dibromostyrene

Mix 3-hydroxybenzaldehyde (2.69 g, 22 mmol), p-methoxybenzyl chloride (2.71 mL, 20 mmol), potassium carbonate (3.04 g, 22 mmol), sodium iodide (1.5 g, 10 mmol) and acetone (60 mL). Heat at reflux for 16 hours, cool to room temperature and remove the solvent in vacuo to give a solid residue. Partition the solid between ethyl ether and 6% sodium hydroxide. Separate the organic phase and filter off any undissolved solid from the organic phase. Dry (MgSO₄), filter and evaporate the solvent in vacuo to yield a solid. Slurry the solid with hexane, filter and air dry to yield 4.10 g (84.6%) of 3-(4-methoxybenzyloxy)benzaldedyde; mp 78°-81° C.

Mix carbon tetrabromide (10.61 g, 32 mmol) and methylene chloride (15 mL), place under argon atmosphere and cool to 0° C. Add, by dropwise addition, a solution of triphenylphosphine (16.77 g, 64 mmol) in methylene chloride (15 mL) and stir at 0° C. for 30 minutes. Add, by dropwise addition, 3-(4-methoxybenzyloxy)benzaldedyde (3.88 g, 16 mmol) in methylene chloride (15 mL). Remove the ice bath and stir at room temperature for 1 hour. Pour onto silica gel and elute with 5% ethyl acetate/hexane. Evaporate the solvent in vacuo to yield a solid. Slurry the solid with hexane, filter and air dry to yield 3.8 g (1st crop) and 0.405 g (2nd crop) of the title compound; mp 76°-9° C.

Step b: 3-(4-Methoxybenzyloxy)phenylacetylene

Place n-butyllithium (9 mL of a 2.5M solution in hexane, 22.5 mmol) and tetrahydrofuran (50 mL) under an argon atmosphere and cool in a dry-ice/acetone bath. Add a solution of 3-(4-methoxybenzyloxy)-2',2'-dibromostyrene (4.25 g, 10.7 mmol) in tetrahydrofuran and stir for 1 hour at low temperature. Remove the cooling bath and stir for 1 hour at room temperature. Pour the yellow solution into saturated aqueous ammonium chloride and extract into ethyl ether. Separate the organic phase, dry (MgSO₄), filter and evaporate the solvent in vacuo to yield a solid. Recrystallize (hexane/chloroform) to yield 1.73 g of the title compound; mp 92°-5° C.

Step c:
1-Phenyl-3-[3-(4-methoxybenzyloxy)phenyl]-2-propyne-1-one

Place lithium hexamethyldisilazane (2 mL of a 1M solution in tetrahydrofuran, 2 mmol) and tetrahydrofuran (8 mL) under an argon atmosphere and cool to 0° C. Add a solution of 3-(4-methoxybenzyloxy)phenylacetylene (0.48 g, 2 mmol) in tetrahydrofuran and stir the brown solution for 45 minutes at 0° C. Add N-methoxy-N-methylbenzamide (0.4 g, 2.4 mmol), remove the cooling bath and stir at room temperature for 1 hour. Partition the mixture between ethyl ether and water, separate the organic phase and dry (MgSO₄). Filter and evaporate the solvent in vacuo to yield an oil. Filter through silica gel and elute with 10% ethyl acetate/hexane to yield a crude solid. Recrystallize (hexane, ethyl ether) to yield 0.26 g (1st crop) and 0.15 g (2nd crop) of the title compound; mp 79°-80° C.

EXAMPLE 3

1-Phenyl-3-[(4-benzyloxy)phenyl]-2-propyne-1-one

Step a: 4-Benzyloxy-2',2'-dibromostyrene

Mix carbon tetrabromide (3.32 g, 10 mmol) and methylene chloride (7 mL), place under argon atmosphere and cool to 0° C. Add, by dropwise addition, a solution of triphenylphosphine (5.24 g, 20 mmol) in methylene chloride (7 mL) and stir at 0° C. for 30 minutes. Add, by dropwise addition, 4-benzyloxybenzaldehyde (1.06 g, 5 mmol) in methylene chloride (10 mL). Remove the ice bath and stir at room temperature for 2 hours. Pour onto silica gel and elute with 5% ethyl acetate/hexane.

Evaporate the solvent in vacuo to yield 1.68 g (91%) of the title compound.

Steps b and c:
1-Phenyl-3-[(4-benzyloxy)phenyl]-2-propyne-1-one

Place 4-benzyloxy-2',2-dibromostyrene (1.68 g, 4.56 mmol) and tetrahydrofuran (15 mL) under an argon atmosphere and cool to −78° C. Add, by dropwise addition, n-butyllithium and stir for 45 minutes at −78° C. Remove the cooling bath and stir for 1 hour at room temperature. Cool the yellow solution to −78° C. and add N-methoxy-N-methylbenzamide (1 mL, 6.6 mmol). Remove the cooling bath and stir at room temperature overnight. Partition between ethyl ether and water, separate the organic phase and dry (MgSO$_4$). Filter and evaporate the solvent in vacuo to yield a solid. Recrystallize (hexane/chloroform) to yield 0.76 g of the title compound; mp 122°–124° C.

EXAMPLE 4

1-(3,4,5-Trimethoxyphenyl)-3-phenyl-2-propyne-1-one

Dissolve 3,4,5-trimethoxybenzoyl chloride (2.3 g, 10 mmol) and N,O-dimethylhydroxylamine hydrochloride (1.10 g, 11 mmol) in ethanol-free chloroform at room temperature. Cool the solution to 0° C. and add pyridine (1.85 g, 22 mmol). Stir at ambient temperature for 1 hour and evaporate the solvent in vacuo. Partition the residue between aqueous sodium chloride and a 1:1 mixture of ethyl ether and methylene chloride. Separate the organic phase, dry (Na$_2$SO$_4$), and evaporate the solvent in vacuo to yield an oil. Filter the oil through silica gel eluting with 65% ethyl acetate/hexane to yield 2.5 g of N-methoxy-N-methyl-(3,4,5-trimethoxy)benzamide.

Place lithium hexamethyldisilazane (3 mL of a 1M solution in tetrahydrofuran, 3 mmol) and tetrahydrofuran (10 mL) under an argon atmosphere and cool to 0° C. Add phenylacetylene (0.33 mL, 3 mmol) and stir at 0° C. for 30 minutes. Add N-methoxy-N-methyl-(3,4,5-trimethoxy)benzamide (0.76 g, 3 mmol), remove the cooling bath and stir at room temperature for 1 hour. Partition between ethyl ether and saturated aqueous sodium chloride, separate the organic phase and dry (MgSO$_4$). Filter and evaporate the solvent in vacuo. Pour onto silica gel and elute with 20% ethyl acetate/hexane to yield a crude solid. Recrystallize (hexane/ethyl acetate) to yield 0.31 g of the title compound; mp 94°–96° C.

EXAMPLE 5

1-Phenyl-3-phenyl-2-propyne-1-one

Place lithium diisopropylamide (10 mL of a 1.5M solution in cyclohexane) and tetrahydrofuran (40 mL) under an argon atmosphere and cool to 0° C. Add, by dropwise addition, phenylacetylene (1.65 mL, 15 mmol). Remove the cooling bath and stir for 30 minutes as room temperature. Cool the yellow solution to 0° C. and add, by dropwise addition, N-methoxy-N-methylbenzamide (3.04 mL, 20 mmol). Remove the cooling bath and stir for 30 minutes at room temperature. Pour onto ethyl ether and water, separate the organic phase and dry (MgSO$_4$). Filter and evaporate the solvent in vacuo to yield an oil. Purify by silica gel chromatography (2% ethyl acetate/hexane) then purify further by distillation (2×) to yield 1.9 g of the title compound; bp 210° C. in vacuo.

EXAMPLE 6

1-Phenyl-3-(3-benzyloxyphenyl)-2-propyne-1-one

Step a: 3-Benzyloxy-2',2'-dibromostyrene

Place carbon tetrabromide (16.6 g, 50 mmol) and methylene chloride (25 mL) under an argon atmosphere and cool to 0° C. Add, by dropwise addition, a solution of triphenylphosphine (26.2 g, 0.1 mol) in methylene chloride (25 mL) and stir at 0° C. for 30 minutes. Add, by dropwise addition, a solution of 3-benzyloxybenzaldehyde (5.31 g, 25 mmol) in methylene chloride (50 mL). Remove the cooling bath and stir at room temperature for 1 hour. Pour onto silica gel (600 mL) and elute with 5% ethyl acetate/hexane to yield 7.4 g, (80.4%) of the title compound.

Step b: 3-Benzyloxyphenylacetylene

Place 3-benzyloxy-2',2'-dibromostyrene (8.2 g, 22.3 mmol) and tetrahydrofuran (70 mL) under argon atmosphere and cool to −70° C. Add, by dropwise addition, n-butyllithium (18.7 mL of a 1.5M solution in hexane, 47 mmol). Stir at −70° C. for 1 hour and then for 1 hour at room temperature. Pour onto ethyl ether and water, separate the organic phase and dry (MgSO$_4$). Filter and evaporate the solvent in vacuo. Purify by preparative liquid chromatography (2% ethyl acetate/hexane) to yield 2.73 g of the title compound.

Step c:
1-Phenyl-3-(3-benzyloxyphenyl)-2-propyne-1-one

Place lithium hexamethyldisilazane (15 mL of a 1M solution in tetrahydrofuran, 15 mmol) and tetrahydrofuran (75 mL) under an argon atmosphere and cool with an ice-water bath. Add, by dropwise addition, a solution of 3-benzyloxyphenylacetylene (3.13 g, 15 mmol) in tetrahydrofuran. Stir at 0° C. for 45 minutes, then add, by dropwise addition, N-methoxy-N-methylbenzamide (2.45 mL, 16 mmol). Remove the cooling bath and stir at room temperature for 1 hour. Partition between ethyl ether and water, separate the organic phase and dry (MgSO$_4$). Filter and evaporate the solvent in vacuo to yield a crude solid. Recrystallize (hexane/ethyl acetate) to yield 2.67 g (57%) of the title compound; mp 75°–77° C.

EXAMPLE 7

1-Phenyl-3-[3-(4-ethoxybenzyloxy)phenyl]-2-propyne-1-one

Step a: 3-(4-Ethoxybenzyloxy)-2',2'-dibromostyrene

Mix 4-ethoxybenzaldehyde (3.3 g, 22 mmol), sodium borohydride (830 mg, 22 mmol) and absolute ethanol (25 mL). Stir at room temperature until the reaction is complete, pour onto dilute hydrochloric acid and extract into ethyl acetate. Separate the organic phase and extract the aqueous phase with ethyl acetate (2×). Combine the organic phases and dry (MgSO$_4$). Evaporate the solvent in vacuo and purify by silica gel chromatography to give 4-ethoxybenzyl alcohol.

Mix 4-ethoxybenzyl alcohol (3.35 g, 22 mmol), 3-hydroxybenzaldehyde (2.69 g, 22 mmol), triphenylphosphine (5.8 g, 22 mmol) and diethylazadicarboxylate (3.83 g, 22 mmol) in tetrahydrofuran (25 mL). Stir at room temperature under anhydrous atmosphere until the reaction is done. Concentrate the solution in vacuo and dilute with a small quantity of ethyl ether. Filter any precipitate and concentrate the filtrate in vacuo.

Purify by silica gel chromatography to give 3-(4-ethoxybenzyloxy)benzaldehyde.

Mix carbon tetrabromide (10.61 g, 32 mmol) and methylene chloride (15 mL), place under argon atmosphere and cool to 0° C. Add, by dropwise addition, a solution of triphenylphosphine (16.77 g, 64 mmol) in methylene chloride (15 mL) and stir at 0° C. for 30 minutes. Add, by dropwise addition, 3-(4-ethoxybenzyloxy)benzaldedyde (4.10 g, 16 mmol) in methylene chloride (15 mL). Remove the ice bath and stir at room temperature for 1 hour. Pour onto silica gel and elute with 5% ethyl acetate/hexane. Evaporate the solvent in vacuo to yield the title compound.

Step b: 3-(4-Ethoxybenzyloxy)phenylacetylene

Place n-butyllithium (9 mL of a 2.5M solution in hexane, 22.5 mmol) and tetrahydrofuran (50 mL) under an argon atmosphere and cool in a dry-ice/acetone bath. Add a solution of 3-(4-ethoxybenzyloxy)-2',2'-dibromostyrene (4.41 g, 10.7 mmol) in tetrahydrofuran and stir for 1 hour at low temperature. Remove the cooling bath and stir for 1 hour at room temperature. Pour the solution into saturated aqueous ammonium chloride and extract into ethyl ether. Separate the organic phase, dry (MgSO$_4$), filter and evaporate the solvent in vacuo to yield the title compound.

Step c: 1-Phenyl-3-[3-(4-ethoxybenzyloxy)phenyl]-2-propyne-1-one

Place lithium hexamethyldisilazane (2 mL of a 1M solution in tetrahydrofuran, 2 mmol) and tetrahydrofuran (8 mL) under an argon atmosphere and cool to 0° C. Add a solution of 3-(4-ethoxybenzyloxy)phenylacetylene (0.51 g, 2 mmol) in tetrahydrofuran and stir the solution for 45 minutes at 0° C. Add N-methoxy-N-methylbenzamide (0.4 g, 2.4 mmol), remove the cooling bath and stir at room temperature for 1 hour. Partition the mixture between ethyl ether and water, separate the organic phase and dry (MgSO$_4$). Filter and evaporate the solvent in vacuo to yield an oil. Filter through silica gel and elute with 10% ethyl acetate/hexane to yield a crude solid. Purify by silica gel chromatography to give the title compound.

EXAMPLE 8

1-Phenyl-3-[3-(4-(dimethylamino)benzyloxy)phenyl]-2-propyne-1-one

Step a: 3-(4-(Dimethylamino)benzyloxy)-2',2'-dibromostyrene

Mix 4-dimethylaminobenzaldehyde (3.3 g, 22 mmol), sodium borohydride (830 mg, 22 mmol) and absolute ethanol (25 mL). Stir at room temperature until the reaction is complete, pour onto dilute hydrochloric acid and extract into ethyl acetate. Separate the organic phase and extract the aqueous phase with ethyl acetate (2×). Combine the organic phases and dry (MgSO$_4$). Evaporate the solvent in vacuo and purify by silica gel chromatography to give 4-(dimethylamino)benzyl alcohol.

Mix 4-(dimethylamino)benzyl alcohol (3.35 g. 22 mmol), 3-hydroxybenzaldehyde (2.69 g, 22 mmol), triphenylphosphine (5.8 g, 22 mmol) and diethylazadicarboxylate (3.83 g, 22 mmol) in tetrahydrofuran (25 mL). Stir at room temperature under anhydrous atmosphere until the reaction is done. Concentrate the solution in vacuo and dilute with a small quantity of ethyl ether. Filter any precipitate and concentrate the filtrat in vacuo. Purify by silica gel chromatography to give 3-(4-(dimethylamino)-benzyloxy) benzaldehyde.

Mix carbon tetrabromide (10.61 g, 32 mmol) and methylenechloride (15 mL), place under argon atmosphere and cool to 0° C. Add, by dropwise addition, a solution of triphenylphosphine (16.77 g, 64 mmol) in methylene chloride (15 mL) and stir at 0° C. for 30 minutes. Add, by dropwise addition, 3-(4-(dimethylamino)benzyloxy)benzaldedyde (4.10 g, 16 mmol) in methylene chloride (15 mL). Remove the ice bath and stir at room temperature for 1 hour. Pour onto silica gel and elute with 5% ethyl acetate/hexane. Evaporate the solvent in vacuo to yield the title compound.

Step b: 3-(4-(Dimethylamino)benzyloxy)phenylacetylene

Place n-butyllithium (9 mL of a 2.5M solution in hexane, 22.5 mmol) and tetrahydrofuran (50 mL) under an argon atmosphere and cool in a dry-ice/acetone bath. Add a solution of 3-(4-(dimethylamino)benzyloxy)-2',2'-dibromostyrene (4.41 g, 10.7 mmol) in tetrahydrofuran and stir for 1 hour at low temperature. Remove the cooling bath and stir for 1 hour at room temperature. Pour the solution into saturated aqueous ammonium chloride and extract into ethyl ether. Separate the organic phase, dry (MgSO$_4$), filter and evaporate the solvent in vacuo to yield the title compound.

Step c: 1-Phenyl-3-[3-(4-(dimethylamino)benzyloxy)phenyl]-2-propyne-1-one

Place lithium hexamethyldisilazane (2 mL of a 1M solution in tetrahydrofuran, 2 mmol) and tetrahydrofuran (8 mL) under an argon atmosphere and cool to 0° C. Add a solution of 3-(4-(dimethylamino)benzyloxy)phenylacetylene (0.51 g, 2 mmol) in tetrahydrofuran and stir the solution for 45 minutes at 0° C. Add N-methoxy-N-methylbenzamide (0.4 g, 2.4 mmol), remove the cooling bath and stir at room temperature for 1 hour. Partition the mixture between ethyl ether and water, separate the organic phase and dry (MgSO$_4$). Filter and evaporate the solvent in vacuo to yield an oil. Filter through silica gel and elute with 10% ethyl acetate/hexane to yield a crude solid. Purify by silica gel chromatography to give the title compound.

Alternatively, compounds of formula (1) can be prepared according to the procedure set forth in Scheme B, wherein all substituents, unless otherwise indicated, are previously described.

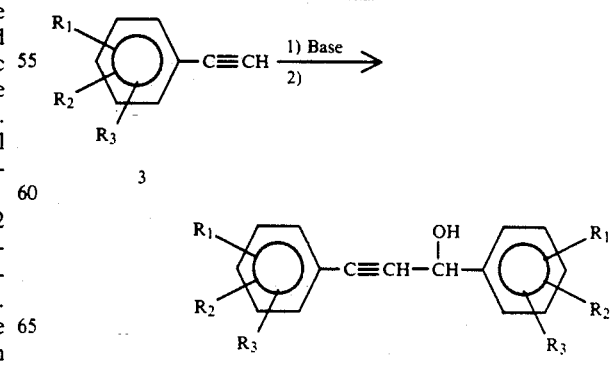

-continued
Scheme B

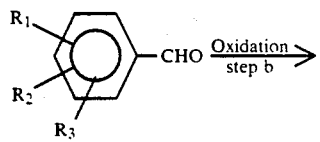

step a

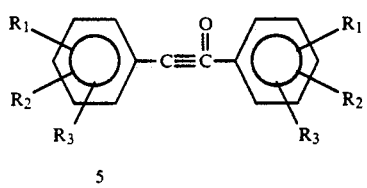

In general, a 1-phenyl-3-phenyl-2-propyne-1-one compound of structure 5 can be prepared in a 2-step process from the appropriate phenylacetylene compound of structure 3 (Scheme A).

In step a, the appropriate α-[(phenyl)ethynyl]-benzenemethanol compound of structure 6 can be prepared by first reacting the appropriate phenylacetylene compound of structure 3 with a non-nucleophilic base, such as n-butyllithium, lithium hexamethyldisilazane, or lithium diisopropylamide, in a suitable aprotic solvent, such as tetrahydrofuran. The corresponding lithium acetylide can then be reacted with the appropriate benzaldeyde compound of structure 1 to give the appropriate α-[(phenyl)ethynyl]-benzenemethanol compound of structure 6.

In step b, the appropriate α-[(phenyl)ethynyl]-benzenemethanol compound of structure 6 can be oxidized to the corresponding 1-phenyl-3-phenyl-2-propyne-1-one compound of structure 5 by techniques and procedures well known and appreciated by one of ordinary skill in the art. For example, the appropriate α-[(phenyl)ethynyl]-benzenemethanol compound of structure 6 can be oxidized to the corresponding 1-phenyl-3-phenyl-2-propyne-1-one compound of structure 5 by means of either a Swern oxidation (dimethylsulfoxide, oxalyl chloride, and triethylamine), by means of pyridinium dichromate oxidation in a suitable aprotic solvent, such as methylene chloride or by means of barium manganate oxidation in a suitable aprotic solvent, such as methylene chloride.

Starting materials for use in the general synthetic procedure outlined in Scheme B are readily available to one of ordinary skill in the art.

The following examples present typical syntheses as described in Scheme B. These examples are understood to be illustrative only and are not intended to limit the scope of the present invention in any way.

EXAMPLE 9

1-(4-Dimethylaminophenyl)-3-(3-benzyloxyphenyl)-2-propyne-1-one

Step a:
1-(4-Dimethylamino)-α-[(3-benzyloxyphenyl)ethynyl]-benzenemethanol

Place lithium hexamethyldisilazane (3 mL of a 1M solution in tetrahydrofuran, 3 mmol) under argon atmosphere and cool to 0° C. Add 3-benzyloxyphenylacetylene (0.62 g, 3 mmol) (see Example 6) in tetrahydrofuran (20 mL) and stir for 1 hour at 0° C. Add a solution of 4-dimethylaminobenzaldehyde (0.42 g, 2.8 mmol) in tetrahydrofuran. Remove the ice bath and stir at room temperature for 1 hour. Pour onto ethyl ether and water, separate the organic phase and evaporate the solvent in vacuo. Filter through silica gel, eluting with 25% ethyl acetate/hexane. Evaporate the solvent in vacuo to yield 0.58 g of the title compound.

Step b:
1-(4-Dimethylaminophenyl)-3-(3-benzyloxyphenyl)-2-propyne-1-one

Mix 1-(4-dimethylamino)-α-[(3-benzyloxyphenyl)ethynyl]-benzenemethanol (0.55 g, 1.5 mmol), pyridinium dichromate (0.75 g, 2 mmol) and methylene chloride (15 mL). Stir at room temperature for 4 hours. Dilute with ethyl ether (100 mL) and filter the solid. Evaporate the solvent and crystallize (hexane/ether) the residual oil. Recrystallize (hexane/chloroform) to yield 0.1 g of the title compound; mp 134°–136° C.

EXAMPLE 10

1-(3-Benzyloxyphenyl)-3-(3-benzyloxyphenyl)-2-propyne-1-one

Step a:
1-(3-Benzyloxy)-α-[(3-benzyloxyphenyl)ethynyl]-benzenemethanol

Place lithium hexamethyldisilazane (1.5 mL of a 1M solution in tetrahydrofuran, 1.5 mmol) under argon atmosphere and cool to 0° C. Add 3-benzyloxyphenylacetylene (0.31 g, 1.5 mmol) (see Example 6) in tetrahydrofuran (10 mL) and stir for 1 hour at 0° C. Add a solution of 3-benzyloxybenzaldehyde (0.32 g, 1.5 mmol) in tetrahydrofuran. Remove the ice bath and stir at room temperature for 1 hour. Pour onto ethyl ether and water, separate the organic phase and evaporate the solvent in vacuo. Filter through silica gel, eluting with 25% ethyl acetate/hexane. Evaporate the solvent in vacuo to yield 0.44 g of the title compound. 339E-175

Step b:
1-(3-Benzyloxyphenyl)-3-(3-benzyloxyphenyl)-2-propyne-1-one

Mix 1-(3-benzyloxy)-α-[(3-benzyloxyphenyl)ethynyl]-benzenemethanol (0.44 g, 1.5 mmol), pyridinium dichromate (0.78 g, 2 mmol) and methylene chloride (15 mL). Stir at room temperature for 4 hours. Dilute with ethyl ether (100 mL) and filter the solid. Evaporate the solvent and purify by silica gel chromatography to yield 0.2 g of the title compound.

The following compounds can be prepared by procedures analogous to those described above in Examples 1–10:
1-Phenyl-3-(3,4,5-triethoxyphenyl)-2-propyne-1-one;
1-Phenyl-3-[4-(4-methoxybenzyloxy)phenyl]-2-propyne-1-one;
1-Phenyl-3-[(3-benzyloxy)phenyl]-2-propyne-1-one;
1-(3,4,5-triethoxyphenyl)-3-phenyl-2-propyne-1-one;
1-(4-Dimethylaminophenyl)-3-(4-benzyloxyphenyl)-2-propyne-1-one;
1-(3-Benzyloxyphenyl)-3-(4-benzyloxyphenyl)-2-propyne-1-one.

One embodiment of the present invention provides a method of inhibiting of calcium uptake in leukocytes. As used herein the term "inhibition" refers to any process whereby the uptake of calcium into leukocytes is slowed, interrupted, arrested, or stopped and does not necessarily indicate a total elimination of calcium uptake into the affected cells or tissues.

The terms calcium and calcium ion ($Ca^{+2}$) may be used interchangably herein to refer to the element of calcium and its ion states which ever may be actively involved the cellular processes of leukocytes. Furthermore, it is understood that inhibition of calcium uptake into leukocytes by compounds of formula (1) may affect one or more of elemental states of calcium and should not be limited to any ionic form of calcium and/or its association with any particular counterion; for example, calcium chloride, calcium carbonate, calcium fluoride, etc. are all known and would be considered within the definition of calcium used herein.

Calcium uptake into leukocytes is one of the signatory events of leukocyte activation and serves as a second messenger to the cell. Often the uptake of calcium is dependent on some first messenger, as for example, the binding of a ligand to its cell surface receptor. Binding of the ligands to their receptors can serve to open $Ca^{+2}$ channels, allowing $Ca^{+2}$ to enter the cytosol, where it then functions as a second messenger. When cells are activated, corresponding to an influx of $Ca^{+2}$ a number of events can occur which lead or contibute to immunological or inflammatory based diseases.

Leukocytes encompass a class of cells of the immune system that are histologically and biochemically distinct from other cells of the immune system. Leukocytes as referred to herein encompass five major classes of cells: neutrophils, basophils, eosinophils, macrophages, and lymphocytes. Within these cell classes can be further classifications of cell types; for example, neutrophils can be further understood to include polymorphonuclear leukocytes. All major classes of leukocytes are related in that they are derived from a progenitor myeloid stem cell. Although the term neutrophil is used extensively herein, it is used to be exemplary of the action of leukocytes as all cells derived from myeloid stem cells and is not meant as any limitation upon the use or administration of compounds of the formula (1) that may be causative or symptomatic from the action of any particular type of leukocytes or cell of the immune system. Furthermore, the action of a leukocytes, wherein the process is to limit or stop the uptake of calcium to affect a cure in a disease process is not limited by the disease being effected by multiple cell or tissue types and encompasses a complex interaction of cellular and tissue interactions. One embodiment of the invention is the inhibition of calcium uptake in leukocytes wherein the effect of inhibition results in a beneficial modulation of phagocytic functions of leukocytes. It is therefore further understood that leukocytic cells can be classified by the functionality inhibited; for example, one could use the term phagocytes or cells with phagocytic functions as a group or subgroup of cells encompassing the cells known as leukocytes herein.

Leukocytes respond to a large variety of inflammatory and immune conditions. During these events receptor activation or general cellular activation results in an altered cellular physiology wherein the leukocyte becomes activated. Often the term "activation" is used to refer to the process or state of leukocytes that have become activated that can be characterized by the cells response to take up calcium while becoming activated or maintaining the state of activation.

The activation of cellular oxidative and nonoxidative mechanisms that result from leukocyte activation play an important role in the development of a number of immune diseases processes. As part of the cellular defense system, including the adverse symptoms and tissue injury of the host, activation of participating leukocytes is in part calcium dependent. The noninfectious disease processes in which leukocytes, primarily the neutrophils, are thought to play an integral part in the symptoms and tissue injury of the host include; gout, rheumatoid arthritis, immune vasculitis, glomerulonephritis, neutrophil dermatoses, inflammatory bowel disease, myocardial infarction, adult respiratory distress syndrome, emphysema, asthma, thermal injury associated with hemolysis, and malignant neoplasms at sites of chronic inflammation (Malech and Gallin; 1987).

In a number of autoimmune diseases, such as gout, autoimmune arthritides, autoimmune vasculitis and some forms of glomerulonephritis, neutrophils are found to accumulate in the areas of the joint and serve to contribute to the destruction of joint and soft tissue. Although a number of disease processes are involved in the patho-physiology of these diseases the recruitment of neutrophils into the area is well documented and may be responsible to a large part of the observable histopathological aspects of these diseases. Therein, a number of studies in model systems have clearly demonstrated that nonoxidative processes which would result from neutrophil activation, particularly the release of neutrophil elastase and other proteolytic and glycolytic enzymes, can directly damage host tissues.

A large variety of dermatopathic disorders are associated with the infiltration of neutrophils into the ectodermal and dermal tissues of the skin. Included with the diseases of the skin wherein neutrophils participate in the progression of the disease, but not limited to, are forms of psoriasiform dermatoses, vessel-based neutrophilic dermatoses as found in Sweet's syndrome and Behcet's disease, and pyoderma gangrenosum. In these disease processes neutrophils serve to augment and maintain the inflammmatory symptoms, enhance tissue injury, and may thereby prevent healing.

A number of other diseases, such as inflammatory bowel disease and myocardial infarction, are related to defective neutrophil function within a particular organ. Studies in animals suggest that abnormalities in the circulation of the neutrophils in the bowel result in an abnormal activation of these cells. In the same sense, neutrophils have been shown to be recruited to the infarction in the myocardial tissues and to play a part in enhancing tissue injury after a myocardial infarction.

The pathogenesis of a number of respiratory disorders including adult respiratory distress syndrome (ARDS), emphysema, and asthma have been associated with neutrophil infiltration and aggravation of the disease. Neutrophil mediated oxidative damage of the pulmonary tissues may be an important component of the pathogenesis of the these respiratory disorders. Further, neutrophil accumulation with the release of elastase may have an important role in the tissue destruction occurring in emphysema and may have an important role in the late phases of the inflammatory response in allergic asthma. The allergic response, during which neutrophils release their constituents, may occur from the release of histamine by mast cells.

Neutrophil activation may serve in the general pathogenesis of diseases related to complement activation. It is well known that complement can serve to activate neutrophils with the concomitant production of hydroxyl radicals. The production of hydroxyl radicals from neutrophil activation may therein be responsible for erythrocyte fragility and intravascular hemolysis associated with complement activation.

The term "inflammation" as used herein is considered as a process that most often involves leukocytes of the immune system and is the process involved in a "inflammatory condition". Clinically, the cardinal signs of inflammation may include one or more of the following symptoms: redness, swelling, heat, pain, loss of function, and fever. However certain cellular events accompanying inflammation include, but not limited to, leukocyte activation, leukocyte margination and emigration, and leukocyte exudation. It is also considered that any condition in which there exist an early or latent inflammatory state, leukocytes may participate in its underlying causes or serve to perpetuate or expand the disease state or condition. Therein, processes involving an inflammatory condition are considered herein to involve leukocytes of the immune system and as such can be viewed within the repertoire of "immune diseases" and conditions affected by leukocytes capable of being treated with compounds of the formula (1). It is also considered that compounds of the present invention that affect the uptake of calcium into leukocytes are thought to be potentially beneficial in the amelioration of conditions involving inflammation and/or immune diseases.

The development of methods like those of the present invention to abrogate neutrophil responses or to inactivate neutrophil oxidative metabolites and granule contents will be useful in limiting tissue destruction in these noninfectious inflammatory diseases.

Platelets (thrombocytes) are non-nucleated cells of the blood that are derived from megakaryocytes of the the bone marrow. Platelets are also required for the clotting of blood and help repair breaches in the walls of blood vessels. The platelet response to form clots and to repair damaged vascular tissue can also have a number of detrimental side effects; for example, during ischemic reperfusion the thrombus formation and associated platelet aggregation can lead eventually to occlusion of the artery. It is also well known in the field that the closing or occlusion of the walls of the arteries and veins can lead to the occurrence of a myocardial infarction. It is also well known that calcium is required in the blood clotting process and for thrombus formation; for example modulation of the clotting response by EDTA and other chelators that bind calcium is firmly established in the field. It is thereby envisioned that inhibiting calcium uptake into platelets may render itself as a viable means by which to modulate platelet activation therapeutically, which would include the release of vasoactive mediators and formation of platelet aggregates, where such use is administered to a patient in need thereof.

As used herein, the term "patient" refers to a warm blooded animal such as a mammal which is afflicted with a particular immune disease state. It is understood that dogs, cats, rats, mice, horses, cattle, sheep, and humans are examples of animals within the scope of the meaning of the term.

The compounds of formula (1) are believed to exert their inhibitory effect on calcium uptake in leukocytes and platelets and thereby provide relief of calcium dependent mechanisms involved in immunoregulation, including inflammatory and immune diseases. However, it is understood that the present invention is not limited by any particular theory or proposed mechanism to explain its effectiveness in and end-use application. It is also understood that the use of the term compounds of the formula (1) is also inclusive of all its radicals that include derivatives (1a), (1b), (1c), and (1d).

As is well known and appreciated by those skilled in the art, various disease states in certain inflammatory and immune diseases are characterized by an events that lead calcium uptake into leukocytes. As used herein, events that lead to calcium uptake in leukocytes can either refer to the initial events leading to the initial condition or events associated with maintaining an inflammatory or immune condition. Furthermore, it is also well known and appreciated by those skilled in the art that certain cardiovascular diseases are characterized by events leading to calcium uptake in platelets and such events may thereto refer either to the initial events leading to the condition or to events associated with maintaining the cardiovascular disease state.

More specifically, the present invention provides a method for the treatment of a patient afflicted with a calcium dependent disease state in leukocytes, wherein such disease states may be, but not limited to, an inflammatory or immune disease, that comprises the administration of a effective calcium uptake inhibitory amount of a compound of formula (1).

A therapeutically effective calcium uptake inhibitory amount of a compound of formula (1) refers to an amount which is effective in controlling the activation of leukocytes involved in a immune disease state. The term "controlling the activation" is intended to refer to all processes wherein there may be a slowing, interrupting, arresting, or stopping of the progression of the immune disease and does not necessarily indicate a total elimination of all disease symptoms.

Furthermore, it is also well known and appreciated by those skilled in the art that certain cardiovascular diseases are characterized by events leading to calcium uptake in platelets and such events may thereto refer either to the initial events leading to the condition or to events associated with maintaining the cardiovascular disease state.

The present invention also provides a method for the treatment of a patient afflicted with a calcium dependent disease state in platelets, wherein such disease states may be, but not limited to, cardiovascular diseases, that comprises the administration of a effective calcium uptake inhibitory amount of a compound of formula (1).

A therapeutically effective calcium uptake inhibitory amount of a compound of formula (1) refers to an amount which is effective in controlling the platelet function involved in a cardiovascular disease state. The term controlling the platelet function involved in a cardiovascular disease refers to slowing, interrupting, arresting, or stopping the progression of the cardiovascular disease and does not necessarily indicate a total elimination of all disease symptoms.

A therapeutically effective inhibitory amount in either a immune or cardiovascular condition or disease, can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of a compound of formula (1) is expected to vary from about 0.1 milligram per kilogram of body weight per day (mg/kg/day) to about 100 mg/kg/day. Preferred amounts are expected to vary from about 0.5 to about 10 mg/kg/day.

In effecting treatment of a patient afflicted with a disease state described above, a compound of formula (1) can be administered in any form or mode which makes the compound bioavailable in effective amounts, including oral and parenteral routes. For example, compounds of formula can be administered orally, subcutaneously, intramuscularly, intravenously, transdermally, intranasally, rectally, topically, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides pharmaceutical compositions comprising a effective amount of a compound of formula (1) in admixture or otherwise in association with one or more pharmaceutically acceptable carriers or excipients. The term "effective calcium uptake inhibitory amount" as applied to compounds of formula (1) refers to effective inhibitory amounts as appropriate to inhibit the uptake of calcium in leukocytes wherein such inhibition may be for a patient suffering from an immune or inflammatory disease. Further the term "effective calcium uptake inhibitory amount" as applied to compounds of (1) also refers to effective inhibitory amounts as appropriate to inhibit the uptake of calcium in platelets wherein such inhibition may be for a patient suffering from a disease associated with the cardiovascular system.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, parenteral, or topical use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The compounds of formula (1) of this invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula 1 or its pharmaceutical salt from about 0.1 to about 10% w/v (weight per unit volume).

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

It is understood herein that the following terms and (abbreviations) used herein are meant to be synonymous with each other: polymorphonuclear leukocytes (PMNL), [4-(2-hydroxyethyl)-1-piperazine-ethanesulfonic acid (HEPES), multiplicative factor of gravity used to express the centrifical force exerted during centrifugation (x g), milliliters (mL), degrees centigrade (°C.), calcium ion ($Ca^{+2}$), nanometers (nm), dimethylsulfoxide (DMSO), ethylenebis (oxyethylenenitrilo)-tetraacetic acid (EGTA) grams (g), milligrams (mg), nanograms (ng), molar (M), millimolar (mM), micromolar (uM), opsonized zymozan (OZ), phorbol myristate acetate (PMA), formyl-methionyl-leucylphenylalanine (fMLP), leukotriene $B_4$ ($LTB_4$).

Compounds are often represented by a three letter abreviation "MDL" a space and a five or six digit extension. Therein it is understood the following representations: 1-phenyl-3-[3-(4 methoxybenzyloxy) phenyl]-2-propyne-1-one (MDL 100,225); 1-phenyl-3-(4-pyridinyl)-2-propyne-1-one (MDL 101,098); 1-(4-dimethylaminophenyl)-3-(4-pyridinyl)-2-propyne-1-one (MDL 102,175); 1-phenyl-3-[(4-benzyloxy)phenyl]-2-propyne-1-one (MDL 101,097); 1-(4-dimethylaminophenyl)-3-(4-pyridinyl)-2-propene-1-one (MDL 101,240); 1-phenyl-3-(4-pyridinyl)-2-propene-1-one (MDL 29,355); 1-(4-diethylaminophenyl)-3-(4-quinolinyl)-2-propyne-1-one (MDL 102,387).

The response of leukocytes to activation signals (stimulants) can be assessed by in vitro measurement of intracellular calcium or by measurement of released factors, such as superoxide anion, and myeloperoxidase. Further the response of leukocytes to stimulation in vivo can be assessed in animal models of edema, such as the mustard oil induced mouse ear edema model and the carrageenin induced rat paw edema model. Inventors of the present subject matter therein demonstrate the method of using the claimed compounds and their utility in the preceding assays.

Materials

Sprague-Dawley rats (150-250 grams) were from Harlan Sprague-Dawley (Indianapolis, Ind.). Hanks' balanced salts (HBSS; Gibco, Grand Island, N.Y.) was supplemented with 20 mM HEPES and adjusted to pH 7.4. Sodium caseinate was from ICN Biochemical (Cleveland, Ohio). Fura-2/AM was from Molecular Probes (Eugene. Oreg.). Ionomycin was from Cal Biochem. (San Diego, Calif.). Superoxide dismutase was from DDI Pharmaceuticals (Mountain View, Calif.). All other reagents were from Sigma Chemical Co. (St. Louis, Mo.). All purchased reagents were used as received.

Isolation of Polymorphonuclear leukocytes (PMNL)

Rat PMNL were obtained from exudates resulting from peritoneal injection of 6 mL of 8% sodium caseinate. Eighteen hours after injection rats were killed by carbon dioxide inhalation and the peritoneal cavity lavaged with Hank's balanced salt solution (HBSS). After concentration of the PMNL by centrifugation, contaminating erythrocytes were removed by hypotonic lysis. The PMNL were then washed twice by centrifugation (400×g for 10 minutes) and resuspended in HBSS. Cell viability was greater than 90% by Trypan Blue exclusion and greater than 90% of the cells were PMNL by Wright-Giemsa stain.

Measurement of Intracellular Calcium

Intracellular calcium levels were obtained using Fura-2 as fluorescent indicator (Grynkiewicz et al., 1985). Fura-2 was loaded into PMNL as the acetoxymethyl ester (Fura-2/AM) using the method of Korchak et al., (1988). Specifically, $1 \times 10^8$ PMNL/mL were incubated in HBSS with 10 μM Fura-2/AM for 10 minutes at 37° C. The cells suspension was then diluted ten fold with HBSS and further incubated for another 20 minutes. The cells were then centrifuged (400×g for 8 minutes at 25° C.) and the PMNL ($1 \times 10^7$ cells/mL) resuspended in HBSS containing 1% bovine serum albumin. Cells were stored at room temperature and used within 3 hours.

Intracellular calcium level determinations were made using a dual wavelength spectrofluorometer (Photon Technology International, New Brunswick, N.J.). Two mL of PMNL suspension ($1 \times 10^7$ cells/mL) were stirred magnetically at 37° C. Cells were preincubated with the compounds for 15 minutes at 37° C. prior to activation. Where compounds were dissolved in DMSO and added directly, the DMSO never exceeded 0.3% in the final cell suspension. Total change in volume with addition of compounds or vehicle and stimuli never exceeded 3%. Intracellular calcium concentrations were calibrated by setting a maximum calcium level in the cells with the addition of 7 uM ionomycin to PMNL in HBSS containing 1% BSA. This was followed by treatment with 20 mM EGTA for 1 hour to obtain a minimum calcium level. The method of Grynkiewiez et al. (1985) was used to quantitate intracellular calcium levels, assuming $K_D$ for Fura-2 to be 240 nM. Each experiment was performed and repeated on three separate occasions and the pattern of calcium changes are representative of these experiments.

Myeloperoxidase (MPO) Release

MPO release was determined using the MPO catalyzed oxidation of o-dianisidine. The experiments were carried out in 96-well microtiter plates (Webster and Henson, 1978). In each well, 50 microliter (μl) aliquots of a PMNL suspension ($2 \times 10^7$ cell/mL in HBSS) were incubated with 50 μl of HBSS containing vehicle (0.3% DMSO) or inhibitor for 30 minutes at 37° C. The final DMSO concentration never exceeded 0.3% and was constant throughout each experiment. To activate the PMNL, 50 μl of one of the following were added for 30 minutes at 37° C.: N-formyl-Met-Leu-Phe (fMLP; 0.1 μM); phorbol myristate acetate (PMA, 200 ng/mL); or rat serum opsonized zymosan (OZ; 2.6 mg/mL, prepared by the method of Ward et al., 1983). The stimuli were added in 50 μl HBSS which also contained the compounds or vehicle, as appropriate, to avoid changing the inhibitor concentration. Cell activation was terminated by centrifugation of the plates at 600×g for 5 minutes at 22° C. Aliquots (100 μl) of supernatant were removed from each well and transferred to a 96-well flatbottomed microtiter plate for the MPO assay. To each aliquot of supernatant was added 100 μl of a freshly prepared solution containing 50 μl of 0.2M sodium phosphate buffer (pH 6.2), 25 μl of 3.9 mM O-dianisidine and 25 μl of 0.015M hydrogen peroxide. Blanks were obtained using the same solution without hydrogen peroxide. The plates were mixed and then incubated at room temperature in the dark for about 15 minutes. Absorbances of the samples were measured at 450 nm.

Superoxide Anion (SOA) Production

Superoxide anion generation was measured using a method comparable to that of Leslie (1987) using microtiter plates, and carried out in presence of catalase (Arthur et al., 1987). Aliquots (50 μl) of a rat PMNL suspension ($2 \times 10^7$ cells/mL in HBSS) were incubated with 50 μl of HBSS containing vehicle (0.3% DMSO) or compound for 30 minutes at 37° C. as above. One hundred microliters of buffer containing 5.98 mg/mL of cytochrome C (Sigma Type III) and 0.1 mg/mL catalase, plus the compounds where appropriate, were then added to each sample. A blank for spectrophotometric measurement, containing unstimulated cells in the presence of cytochrome C, catalase and SOD, was also prepared. To activate the PMNL, 75 μl of PMA or OZ were added to achieve the final concentration of cell activator (plus vehicle or inhibitor as described above for MPO release) and the cells further incubated at 37° C. for 60 minutes. The activation was terminated by centrifugation at $600 \times g$ for 5 minutes at 4° C. Aliquots (200 μl) of supernatant were then transferred to a second, flat-well microtiter plate and measured spectrophotometrically at 550 nm.

EXAMPLE 11

Effect of Various Stimuli on PMNL Intracellular Calcium

Rat PMNL preloaded with Fura-2 were stimulated with fMLP and levels of intracellular calcium were followed as shown in FIG. 1. The chemotactic peptide fMLP produced a biphasic response with a first peak reaching a maximum after 30 seconds and a second peak maximizing around 100 seconds after giving the peptide stimulus.

The biphasic response is consistent with those seen by Korchak et al., (1986) for human neutrophils wherein the peak of the response corresponds to an early release of intracellular calcium, as would be produced from a response with $LTB_4$. The second phase of the response, corresponding to the second peak at about 100 seconds after stimulation, is associated with an influx of extracellular calcium, typical from a Concanavalin A induced response. The biphasic response is interpreted by those skilled in the art to mean that the first phase is the release of intracellular calcium and the second phase corresponds to the influx of extracellular calcium.

Preincubation of PMNL with MDL 101,097 shown in FIG. 1 resulted in the selective concentration-dependent suppression of the second wave of intracellular calcium changes. The inhibition of the second peak of the response by compounds of formula (1), as represented by the activities of MDL 101,097, can be seen to effective inhibit the calcium uptake of the treated PMNL. At high concentrations (>100 μm), however, compounds did begin to affect the first phase (data not shown). The control response, whereno compounds of formula (1) are included in the fMLP stimulus, shows the observed biphasic response.

EXAMPLE 12

Effect of Compounds on Rat PMNL Enzyme Release and Superoxide Anion Generation Rat PMNL were isolated in HBSS containing $Ca^{+2}$. As summarized in the table below, fMLP stimulation of rat PMNL in the presence of cytochalasin B or with opsonized zymosan or with ionomycin results in the release of myeloperoxidase (fMLP/MPO, OZ/MPO, and ION/MPO; columns 2, 4, and 6 respectively). Addition of MDL 102,175 shows a dose dependent inhibition of both responses at the given concentrations. Similarly, PMA and OZ results in superoxide anion production which is inhibited in a dose dependent fashion by the addition of MDL 101,098 (PMA/SOA and OZ/SOA; columns 8 and 10 respectively). These data are also consistent with the affect that one would see if rat PMNL were deprived of extracellular calcium (data not shown).

| EFFECT OF STIMULI ON MDL 101,098 INHIBITION OF RAT PMN MPO AND SOA | | | | | | | | | | |
|---|---|---|---|---|---|---|---|---|---|---|
| 1 CONC (uM) MDL 101.098 | 2 fMLP/MPO | 3 SEM | 4 OZ/MPO | 5 SEM | 6 ION/MPO | 7 SEM | 8 PMA/SOA | 9 SEM | 10 OZ/SOA | 11 SEM |
| 100 | 96.2 | 1.8 | 97.2 | 4.5 | 88.4 | 4.1 | 97.2 | 2.3 | 115.0 | 10.1 |
| 30 | 80.8 | 9.0 | 92.2 | 1.1 | 12.7 | 2.7 | 70.0 | 10.3 | 61.5 | 8.3 |
| 10 | 34.9 | 5.7 | 48.7 | 8.6 | 5.7 | 2.5 | 29.1 | 5.8 | 20.3 | 5.0 |
| 3 | 7.5 | 6.1 | 14.7 | 7.7 | 0.0 | 1.3 | −4.3 | 10.6 | −7.5 | 6.6 |
| 1 | 2.9 | 4.4 | 5.4 | 10.9 | −2.8 | 0.7 | −20.7 | 7.9 | −18.0 | 3.9 |

SEM is the standard error of the mean for the preceding numbered experiment.

EXAMPLE 13

Mustard Oil-Induced Mouse Ear Edema

Charles River male CD-1 mice weighing 30-60 grams were divided into randomized groups. They were dosed i.p. for 30 minutes prior or orally 1 hour prior to application of 20 ul of mustard oil (10% isothiocyanate in acetone) to the right ear. After 30 minutes the mice were sacrificed and an 8 millimeter diameter circular punch biopsy of each ear was obtained and weighed. The difference between the left (control) and right (treated) ear weights were expressed as percent increase. Results of the Mustard Oil Induced Mouse Ear Edema Test are shown in the table below.

| MUSTARD OIL INDUCED MOUSE EAR EDEMA | | | |
|---|---|---|---|
| COMPOUND | DOSE (mg/Kg) | Route | % Inhibition |
| MDL 100,225 | 100 | i.p. | 60.9 ± 11.7 |
|  | 30 |  | 33.4 ± 14.6 |
|  | 10 |  | 25.3 ± 17.8 |

EXAMPLE 14

Carrageenin-Induced Rat Paw Edema

Charles River male Sprague Dawley rats weighing 90 to 100 grams were used. Inflammation of the left hind paw was induced by a 1% carrageenin solution (0.05 cc), injected into the plantar surface of the paw. The contralateral paw was injected with an equal volume of saline. Drugs were administered 75 mg/Kg i.p. (1 cc/100 grams) one hour prior to paw injection. Three hours following the carrageenin injection the difference in volume of the control and inflamed paw was measured. Each paw was immersed in a well of mercury and the volume of mercury displaced was recorded. Paws were uniformly dipped into the mercury up to the beginning of the hairline. A venous pressure transducer, coupled to an chart recorder, was employed to measure the small volumes of mercury displaced. Each group measurement consists of the average of four rats, each with three separate measurements. Results of the Carrageenin Induced Rat Paw Edema test are shown in the table below.

| CARRAGEENIN INDUCED RAT PAW EDEMA | | |
|---|---|---|
| Compounds | Route | % Inhibition |
| MDL 100.225 | i.p. | 24.3% ± 10.3% |

What is claimed is:

1. A compound selected from formula 1:

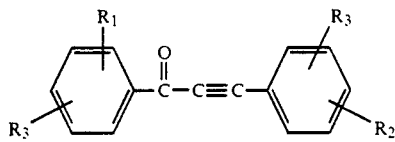

wherein $R_1$, $R_2$ may each time independently be:
hydrogen,
$-N(Y_1)(Y_2)$, wherein $Y_1$ is hydrogen or $C_1-C_6$ alkyl, and $Y_2$ is a $C_1-C_6$ alkyl, or
$X_z-(Ar)-(CH_2)_n-O-$, wherein Ar is phenyl or napthyl, $n=0$ or 1, $X_z=$hydrogen, $C_1-C_6$ alkoxy or $-N(Y_1)(Y_2)$, wherein $Y_1$ and $Y_2$ are as previously defined and $Z=0, 1, 2$;
with the provision that $R_1$, and $R_2$, may not simultaneously be hydrogen; and
$R_3$ is each time independently hydrogen, halogen, $C_1-C_6$ alkyl, or $C_1-C_6$ alkoxy;
or the compounds of formula 1 may be a pharmaceutically acceptable salt thereof.

2. A compound of claim 1 wherein the compound is 1-phenyl-3-(3,4,5-trimethoxyp[r]henyl)-2-propyne-1-one.

3. A compound of the structure 1-phenyl-3-[3-methoxybenzyloxy)phenyl]-2-propyne-1-one.

4. A compound of claim 1 wherein the compound is 1-phenyl-3-[(4-benzyloxy)phenyl]-2-propyne-1-one.

5. A compound of the structure 1-(3,4,5,-trimethoxyphenyl)-3-phenyl-2-propyne-1-one.

6. A compound of claim 1 wherein the compound is 1-phenyl-3-(3-benzyloxyphenyl)-2-propyne-1-one.

7. A compound of claim 1 wherein the compound is 1-(4-dimethylaminophenyl)-3-(3-benzyloxyphenyl)-2-propyne-1-one.

8. A compound of claim 1 wherein the compound is 1-(3-benzyloxyphenyl)-3-(3-benzyloxyphenyl)-2-propyne-1-one.

9. A compound of the structure 1-phenyl-3-[4-(ethoxybenzyloxy)phenyl]-2-propyne-1-one.

10. A compound of claim 1 wherein the compound is 1-phenyl-[3-(4-dimethylamino)benzyloxy)phenyl]-2-propyne-1-one.

* * * * *